United States Patent [19]

Stewart

[11] Patent Number: 4,793,331

[45] Date of Patent: Dec. 27, 1988

[54] SHOWER FLOSSING SYSTEM

[76] Inventor: Clyde F. Stewart, 26300 Hickory Blvd. SW, Apt. 1105, Bonita Springs, Fla. 33923

[21] Appl. No.: 152,870

[22] Filed: Feb. 5, 1988

[51] Int. Cl.[4] .............................................. A61H 9/00
[52] U.S. Cl. ......................................... 128/66; 4/615
[58] Field of Search ............................. 128/66; 4/615

[56] References Cited

U.S. PATENT DOCUMENTS

| | | | |
|---|---|---|---|
| 2,112,145 | 3/1938 | Courtney | 604/150 |
| 2,173,979 | 9/1939 | Picut | 251/122 |
| 2,507,214 | 5/1950 | Medley | 128/229 |
| 2,550,565 | 9/1948 | Hyser | 128/229 |
| 3,499,440 | 3/1970 | Gibbs | 128/66 |
| 3,500,824 | 3/1970 | Gilbert | 128/66 |
| 3,771,517 | 11/1973 | Radecki | 128/66 |
| 3,820,532 | 6/1974 | Eberhardt et al. | 128/66 |
| 3,870,045 | 3/1975 | Vaughan | 128/229 |
| 3,966,359 | 6/1976 | Woog | 128/66 |
| 3,973,558 | 8/1976 | Stouffer et al. | 128/66 |
| 4,043,337 | 8/1977 | Baugher | 128/66 |
| 4,265,229 | 5/1981 | Rice et al. | 128/66 |
| 4,269,222 | 5/1981 | Palti | 251/122 |
| 4,269,387 | 5/1981 | Reynolds | 251/122 |
| 4,538,646 | 9/1985 | Yand | 4/192 |
| 4,564,005 | 1/1986 | Merchand et al. | 128/66 |

Primary Examiner—John J. Wilson
Attorney, Agent, or Firm—Merrill N. Johnson

[57] ABSTRACT

Apparatus including an oral syringe for attachment to a shower head for cleaning the teeth and gums while showering. The oral syringe is connected to water flowing under pressure to the shower head through a unique valving assembly which diverts a manually adjustable portion of the water flowing to the shower head into a passageway lying at right angles to the direction of the flow of the water into the shower head. A manually adjustable valve stem including an O-ring valve is located in the passageway and controls the flow of water through an axial passageway in the valve stem. A flexible hose connected to the rear end of the valve stem conveys the water to the oral syringe. The valve stem also controls a diverter valve which can be adjusted to cut off the flow of water to the shower head in the event of low water line pressure to insure sufficient water pressure to the oral syringe for proper cleaning of the teeth and gums.

7 Claims, 1 Drawing Sheet

SHOWER FLOSSING SYSTEM

BACKGROUND AND SUMMARY OF THE INVENTION

My invention relates generally to the field of dental hygiene and particularly to an adjustable oral syringe which can deliver a jet stream of water for cleaning the teeth and gums of a person while showering which I call The Shower Floss TM.

Numerous methods and apparatus have been suggested for cleaning the teeth and gums by using a jet stream of water. One widely accepted system involves the use of a pulsing jet of water fed to a hand-held syringe by an electrically driven pump placed beside a bathroom was basin or sink. This system requires a relatively expensive electrically driven pumping mechanism and has the further disadvantages of taking up space on the user's bathroom sink and splashing up the bathroom mirror and sink during its use.

It has also been suggested that it would be less time consuming, less expensive, less messy and also more enjoyable to clean the teeth and gums with a stream of water in a shower stall rather than over a wash basin or sink. Three widely different forms of apparatus designed to utilize an oral syringe in a shower stall are shown in U.S. Pat. Nos. 4,043,337, 4,265,229 and 4,564,005. However, so far as I am aware, no oral syringe for cleaning the teeth and gums in a shower stall appeared on the market until the introduction of my Shower Floss TM.

I have invented a unique system for cleaning the teeth and gums while at the same time cleansing the body under a shower of water. My apparatus permits immediate manual adjustment of the intensity of the stream of water projected from the syringe. In its preferred form, the apparatus can easily be installed in any existing shower stall in a matter of minutes and its cost to the home owner is considerably less than the cost of oral syringes used on bathroom wash basins and powered by electrically driven pulsing pumps.

My system is total leak-proof, thus insuring that the pressure of the water flowing to the restrictions in the shower head which create the pressure used both by the shower head itself and the oral syringe is not diminished by leaks in the valving mechanism used to divert a portion of the water away from the shower head and into the oral syringe. Moreover, my system includes a diverter valve which can be manually adjusted to cut off the flow of water to the shower head completely in the event of low water line pressure to insure sufficient water pressure to the oral syringe for proper cleaning of the teeth and gums.

The foregoing features are the result of the unique arrangement of my valving system. The water to be used by the oral syringe is diverted from the water flowing through an adapter to the shower head into a passageway lying at right angles to the direction of flow to the shower head. A thumb-and-finger operated o-ring valve mounted on a valve stem at the end of this passageway controls the flow of water from the passageway into an axial passageway in the valve stem which leads through a flexible hose to the oral syringe. Being connected to the valve stem by a flexible hose, the syringe is freely manueverable in the hand of the person using the syringe and at the same time using the shower head.

BRIEF DESCRIPTION OF THE DRAWINGS

The numerous benefits of my invention will become apparent from the following description of a preferred embodiment and the attached drawings in which.

DETAILED DESCRIPTION OF A PREFERRED EMBODIMENT

Figure 1:
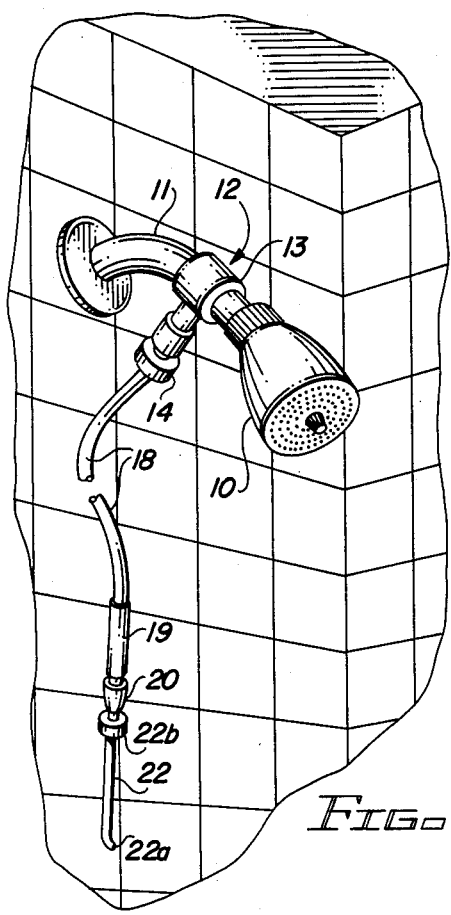
FIG. 1 is a perspective view of my adjustable oral syringe installed in a conventional shower stall.

Referring first to FIG. 1, a shower stall includes a conventional shower head 10 which receives water under pressure from inlet pipe 11. My shower flossing assembly 12 is coupled to the shower head 10 by adapter 13, which is connected between pipe 11 and shower head 10.

Figure 2:
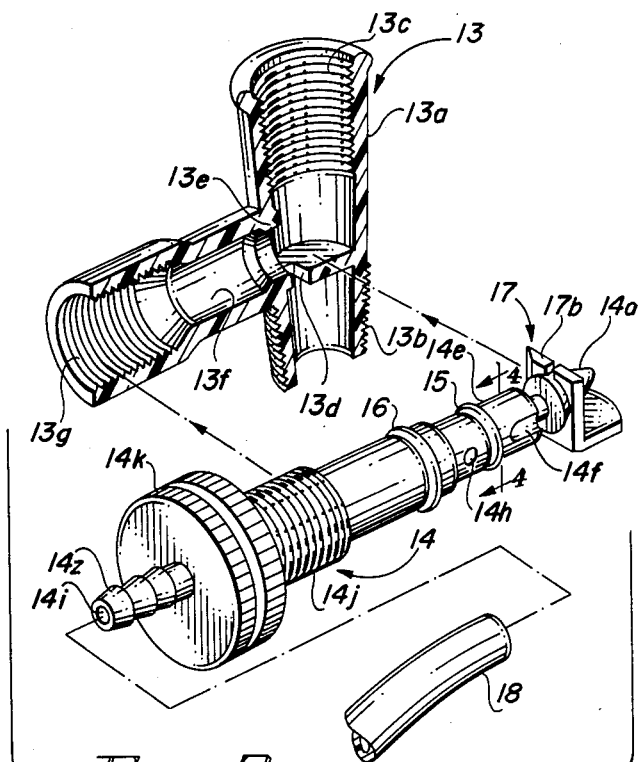
FIG. 2 is an exploded view partially in cross-section of the adapter and the manually adjustable valve stem shown in FIG. 1.

Water flowing through inlet pipe 11 is kept close to line pressure due to the restrictions which form the shower of individual water jets flowing from shower head 10. My unique valving arrangement provided by adapter 13 and valve stem 14, best shown in FIGS. 2, 3 and 4, diverts a manually adjustable portion of the water flowing toward the shower head to oral syringe 22 for cleaning the teeth and gums of the person taking a shower.

Adapter 13 is preferably made of high density thermoplastic material such as acetal thermoplastic. Its main body 13a contains a generally cylindrical passageway with internal threads 13c sized to accommodate the end of pipe 11 and external threads 13b sized to mate with shower heat 10. Adapter main body 13 also contains a restricted rectangular passageway or port 13d shown in FIG. 2.

An extension projects at right angle from the housing's main body 13a and contains a passageway 13f running at right angle to the passageway in main body 13a. A thumb-and-finger operated valve stem 14 is screwed into internal threads 13g in the end of the adapter extension. Valve stem 14 is preferably made of thermoplastic material and includes thumb-and-finger operated knurled knobs 14k and external threads 14j which mesh with internal threads 13g of the adapter extension.

Figure 3:
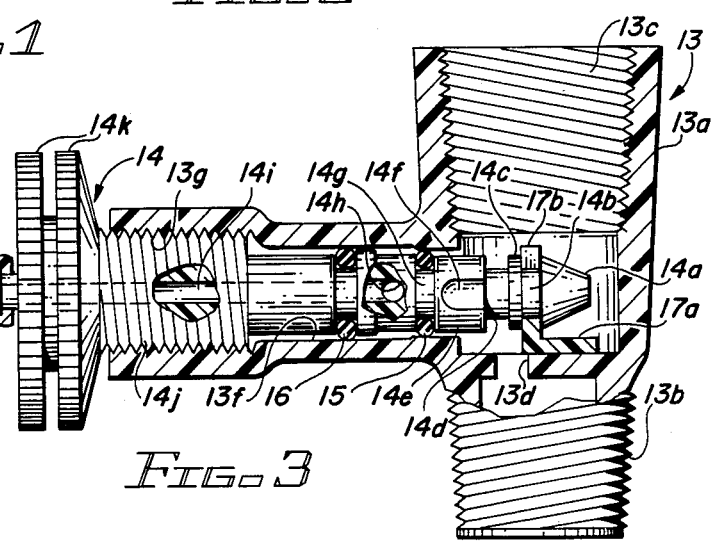
FIG. 3 is a side view partially in cross-section of the adapter and the valve stem shown in FIG. 2.

Valve stem 14 includes a truncated conical nose 14a and a narrow groove 14b formed by the rear of nose 14a and the front face of annular flange 14c best shown in FIG. 3. Groove 14b is sized to receive diverter valve 17. Valve stem portion 14d is narrowed to permit free flow of water around the valve stem and through port 13d to shower head 10.

Figure 4:
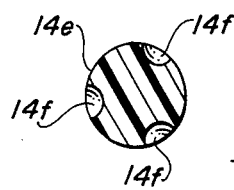
FIG. 4 is a cross-sectional end view of the three grooves in the valve stem shown in FIGS. 2 and 3.
Figure 5:
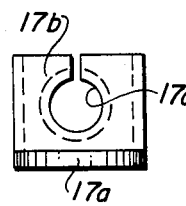
FIG. 5 is a detailed view of the diverter valve shown in FIGS. 2 and 3.

Valve stem segment 14e contains three similar grooves 14f best shown in FIGS. 3 and 4. Directly behind segment 14e is an annular groove 14g into which is fitted O-ring valve 15 made of waterproof resilient material. When valve stem 14 is screwed manually forward the O-ring is pressed tightly into the somewhat narrower forward end of passageway 13f, thus cutting off completely the flow of water into the wider portion of passageway 13f.

However, when valve stem 14 is retracted so valve 15 is moved out of the narrowed portion of passageway 13f, water will flow along the grooves 14f into passageway 13f and thence through hole 14h and into axial passageway 14i in the rear portion of valve stem 14 as shown in FIG. 3. A flexible hose 18 preferably of clear plastic is firmly attached to the rear of valve stem 14 by barbed valve stem extension 14z. A second O-ring 16 also of resilient waterproof material but somewhat larger than O-ring valve 15 is fitted into a second groove in the valve stem and acts as a seal to prevent water leaking along the threads 14j of the valve stem. O-rings 15 and 16 are preferably lubricated with silicon grease to improve their respective valving and sealing functions. I have found after many hours of continuous operation and months of daily use that the foregoing valving arrangement is entirely leak-proof and provides incremental control of the rate of flow of water to the oral syringe.

In the event of low water line pressure to provide both a proper shower and flossing of the teeth and gums, my apparatus provides means for cutting off the flow of water to the shower head 10 and diverting all the water to the flossing syringe. Diverter valve 17 attached to valve stem 14 consists of an L-shaped plastic member with a flat smooth-surfaced plate 17a and at right angle of flange 17b split at its top to form a cylindrical hole 17c sized to fit over groove 14b of the valve stem. When valve stem is "backed off" or retracted beyond the normal opening of O-ring valve 15, the lower flat face of diverter valve 17 is drawn over port 13d to close off the flow of water to shower head 10.

Figure 6:
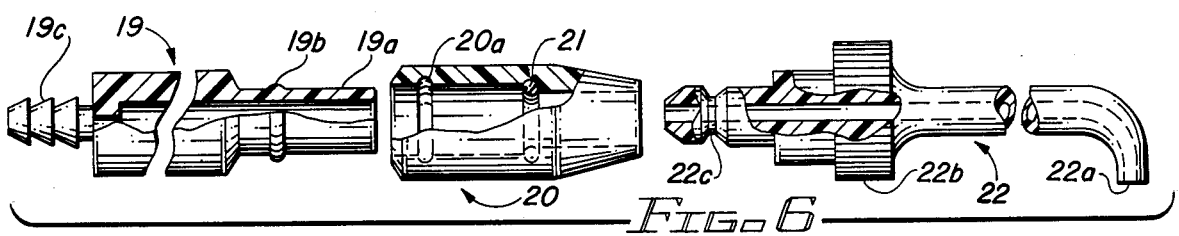
FIG. 6 is an exploded view partially in cross-section of a preferred form of the handle and nozzle of the oral syringe shown in FIG. 1.

One end of flexible hose 18 is connected to barbed valve stem extension 14z and its other end is connected to the barbed end 19c of syringe handle 19 as shown in FIGS. 1 and 6. Handle extension 20 is fitted onto the front end 19a of the handle and held in place by annular ring 19b fitting into groove 20a in handle extension 20.

Oral syringe 22 fits onto the front end of handle extension 20 and is held in place but with freedom to rotate about its axis by O-ring 21 made of waterproof resilient material resting within groove 22c in the syringe. By finger tip control of knurled ring 22b the user may direct the jet of water from nozzle tip 22a in any desired direction.

In operation, with oral syringe assembly 12 connected between water inlet pipe 11 and shower head 10 as shown in FIG. 1, valve stem 14 is normally screwed inwardly so that O-ring valve 15 is just fully within the restricted inner end of passageway 13f to seal off that passageway. Thus when the shower is first turned on all the water flowing from inlet pipe 11 flows to the shower head.

Then when the person taking a shower wishes to continue showering and at the same time floss his or her teeth and gums, the person first uses a thumb and finger to rotate knurled knob 14k counterclockwise to move valve 15 out of engagement with the wall of passageway 13f to feed the desired amount of water through grooves 14f into passageway 13f, thence through hole 14h and into axial passageway 14i and into hose 16, through handle 19, hendle extension 20 and syringe 11 and out of nozzle tip 22a as a fine jet of water for flossing the teeth and gums.

For those persons who desire a pulsing jet of water for flossing, pulsing mechanism can be included in my apparatus, either within the adapter 13, the valve stem 14 or the handle 19.

It will be apparent to those skilled in the art that various modifications of the valving structure herein shown and described may be made without departing from the scope and spirit of my invention. For example, adapter 13 could be eliminated and valve stem 14 mounted directly onto the rear portion of the shower head itself and still achieve the advantages of invention. Accordingly, my invention is limited only by the appended claims.

I claim:

1. In a system for attaching an oral syringe to a shower head, means for diverting to the syringe a manually adjustable portion of the water flowing to the shower head comprising an adapter having one end which is connected to the water supply pipie and an opposite end which is connected to the shower head, the adapter having a passageway lying between its opposite ends and at right angle to the direction of flow of water to the shower head, a thumb-and-finger operated valve stem threadedly located partially within the passageway of the adapter, said valve stem having within its rear portion an axial passageway whose one end is connected to the passageway within the adapter and whose other end is connected to the oral syringe, and an O-ring valve of waterproof resilient material mounted in a groove on the valve stem for controlling the flow of water into the passageway within the adapter by rotating the valve stem to change the position of the O-ring valve.

2. In a system for attaching an oral syringe to a shower head as set forth in claim 1, wherein the adapter includes a restricted port for the passage of water flowing to the shower head, and a diverter valve attached to the valve stem and movable therewith for covering the port in the adapter by retraction of the valve stem away from the closed position of the O-ring valve.

3. In a system for attaching an oral syringe to a shower head as set forth in claim 1, wherein a second O-ring of waterproof resilient material is mounted in a second groove on the valve stem for sealing the passageway within the adapter to prevent water from leaking along the threads of the valve stem.

4. In a system for attaching an oral syringe to a shower head as set forth in claim 1, wherein the valve stem includes a disk-shaped knob near its rear end for thumb-and-finger rotation of the threaded valve stem.

5. In a system for attaching an oral syringe to a shower head as set forth in claim 1, wherein the valve stem includes three similar grooves lying parallel to the axis of the valve stem forward of the O-ring valve to channel water into the passageay when the O-ring valve is retracted.

6. In a system for attaching an oral syringe to a water line under pressure, means for diverting to the syringe a manually adjustable portion of the water flowing through the line comprising an adapter whose opposite ends are connected to the water line and having a passageway midway between its opposite ends lying at right angle to the direction of flow of water through the adapter, a thumb-and-finger operated valve stem threadedly located at least partially within the passageway of the adapter, said valve stem having within its rear portion an axial passageway whose one end is connected to the passageway within the adapter and whose opposite end is connected to a flexible hose leading to the oral syringe, and a resilient O-ring valve positioned on the valve stem to control the amount of water flowing into the passageway and hence to the oral syringe.

7. In a system for attaching an oral syringe to a water line under pressure as set forth in claim 6 wherein a second resilient O-ring is mounted on the valve stem to seal the passageway within the adapter and prevent water from leaking along the threads of the valve stem.

* * * * *